US005616281A

United States Patent [19]

Hardy et al.

[11] Patent Number: 5,616,281
[45] Date of Patent: *Apr. 1, 1997

[54] ACYLATED CITRATE ESTERS AS PERACID PRECURSORS

[75] Inventors: Frederick E. Hardy; Alan D. Willey, both of Newcastle upon Tyne, Great Britain; Stefano Scialla, Rome, Italy

[73] Assignee: The Procter & Gamble Company, Cincinnati, Ohio

[ * ] Notice: The term of this patent shall not extend beyond the expiration date of Pat. No. 5,409,632.

[21] Appl. No.: 244,470

[22] PCT Filed: Dec. 4, 1992

[86] PCT No.: PCT/US92/10455

§ 371 Date: Nov. 9, 1994

§ 102(e) Date: Nov. 9, 1994

[87] PCT Pub. No.: WO93/12067

PCT Pub. Date: Jun. 24, 1993

[30] Foreign Application Priority Data

Dec. 13, 1991 [EP] European Pat. Off. .............. 91870207

[51] Int. Cl.$^6$ .............. C09K 3/00; C11D 3/395
[52] U.S. Cl. ...................... 252/186.38; 510/312
[58] Field of Search ................... 560/146, 180, 560/103, 104, 181, 182; 252/186.38, 186.25, 95; 554/227; 510/312

[56] References Cited

U.S. PATENT DOCUMENTS

| 3,025,271 | 3/1962 | Borchert ................... 260/78.3 |
| 3,936,303 | 2/1976 | Shiba et al. ............... 96/74 |
| 4,287,741 | 9/1981 | Peters et al. ............... 72/42 |
| 4,772,290 | 9/1988 | Mitchell et al. ............ 8/107 |
| 4,800,038 | 1/1989 | Broze et al. ............... 510/276 |
| 4,892,967 | 1/1990 | Hull et al. ................. 560/180 |
| 4,931,583 | 6/1990 | Hull et al. ................. 560/180 |
| 5,011,661 | 4/1991 | Schafer et al. ............. 422/30 |
| 5,102,575 | 4/1992 | Lanniel et al. ............. 252/186.29 |
| 5,320,775 | 6/1994 | Harirchian et al. ......... 252/186.38 |
| 5,409,632 | 4/1995 | Showell et al. ............ 252/186.23 |

Primary Examiner—Sharon Gibson
Assistant Examiner—Joseph D. Anthony
Attorney, Agent, or Firm—Kim William Zerby; Jacobus C. Rasser; Brian M. Bolam

[57] ABSTRACT

The present invention relates to acylated citrate esters to be used as peracid precursors in a bleaching or a disinfecting operation. The present invention encompasses the use of these acylated citrate esters, granular or liquid compositions comprising the acylated citrate esters. Activating compositions are described as well as activated bleaching compositions.

19 Claims, No Drawings

ACYLATED CITRATE ESTERS AS PERACID PRECURSORS

TECHNICAL FIELD

The present invention relates to the use of certain acylated citrate esters as peracid precursors in a bleaching or a disinfecting operation.

BACKGROUND OF THE INVENTION

Bleaching operations using hydrogen peroxide or compounds capable of yielding hydrogen peroxide, hereinafter referred to as peroxygen bleaches, have been extensively described in the art. Such peroxygen bleaches have an advantage over chlorine bleaches, in that they are milder bleaches. This advantage is especially significant in the context of a fabric laundering operation because peroxygen bleaches are safer to fabric colors and are non-yellowing to white fabrics.

A major drawback of peroxygen bleaches is that they are less active than chlorine bleaches at low temperatures which are often encountered in modern laundering operations, or in the treatment of hard surfaces. Thus, peroxygen bleach activators have been developed, which have been extensively addressed in the art. These activators can be transition metal or peracid precursors. Peracid precursors react with hydrogen peroxide to yield peracids. Peracids are the "activated" bleaching species which are efficient at low temperatures.

Such peracid-yielding systems are also of interest in non-laundry applications, as they provide disinfectancy benefits in addition to some bleaching benefits, due to the peracid. Such benefits are particularly desirable on kitchen and bathroom surfaces, especially in toilet bowls.

Peroxygen type bleaches are also advantageous over chlorine bleaches in terms of environmental compatibility, and there is a continuous need for the development of products which are ever more environmentally compatible. Specifically, there is a need to develop environmentally compatible peracid precursors.

In addition, products comprising both a peroxygen bleach and an activator need to meet a balance between shelf-stability of that combination, and its capability to react as fast as possible in water, during the bleaching operation. These two characteristics are somewhat contradictory. This problem is especially acute in liquid aqueous compositions, but it also exists in dry products where shelf stability can become an issue if the product is subjected to humid environments, as the product can become damp and may lose some activity.

EP 241 137 proposes to use solid peracid precursors which are insoluble in an acidic aqueous medium, but become soluble in an alkaline medium. Such a system is said to be stable upon storage, but all activators proposed therein comprise benzene rings and are therefore not particularly environmentally compatible.

EP 210 674 proposes P-sulphophenyl carbonates as hydrogen peroxide activators. All these compounds comprise phenyl groups, thus are not environmentally compatible.

EP 396 287 teaches pH control in a bleaching process using hydrogen peroxide and a peracid precursor, wherein the wash pH is initially raised, then lowered to promote bleach efficiency. That document contains an exhaustive list of the peracid precursors described in the art.

It has now been found that the acylated citrate esters according to the present invention would meet all the objects described hereinabove. The acylated titrate esters according to the present invention are fully environmentally compatible as they eventually degrade into citric acid and alcohols. They are particularly stable upon storage in a mildly acidic medium, compared to the activators of the art, even in a liquid composition comprising a peroxygen bleach.

Some of the acylated citrate esters according to the present invention also provide an additional benefit in that they exhibit interesting building capacity. Such benefit is particularly useful in the context of a laundering application.

The acylated citrate esters according to the present invention thus allow great flexibility in that they can be used in any product, granular or liquid, with or without a peroxygen bleach.

SUMMARY OF THE INVENTION

The present invention encompasses a composition for use in a bleaching or disinfecting operation, comprising a peracid precursor, characterized in that the peracid precursor is an acylated citrate ester of the formula:

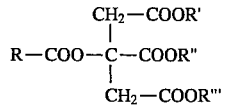

wherein R is selected from a $C_{1-9}$ alkyl or alkenyl group, a substituted or unsubstituted phenyl, alkylphenyl, or alkenylphenyl group, R', R" and R''' are selected from H, $C_{1-18}$ alkyl or alkenyl group, a substituted or unsubstituted phenyl, alkylphenyl or alkenyl phenyl group, with the proviso that R', R" and R''' are not all H, or mixtures of said activators.

The present invention encompasses granular or liquid activating compositions comprising said acylated citrate esters, activated bleaching compositions comprising said acylated citrate esters and hydrogen peroxide or a hydrogen peroxide generating compound as well as the use of said acylated citrate esters as hydrogen peroxide activators. In a preferred embodiment, the acylated citrate esters according to the present invention are formulated in an acidic aqueous bleaching composition comprising hydrogen peroxide.

DETAILED DESCRIPTION OF THE INVENTION

1) The acylated citrate esters

The acylated citrate esters the present invention proposes to use as peracid precursors are of the formula

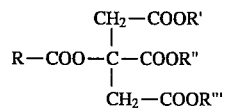

In the bleaching or disinfecting operation, the acylated citrate esters according to the present invention will react with hydrogen peroxide to yield peracids and citrate esters. The peracid generated depends on the R group which is chosen and R is selected from a $C_{1-9}$ alkyl or alkenyl group, a substituted or unsubstituted phenyl, alkylphenyl, or alkenylphenyl group. Preferred substituted phenyls are sulpho phenyls. Preferably, R is methyl or heptyl, most preferably methyl. In this case, the acylated citrate esters yield peracetic acid, the efficiency of which is well known.

R', R" and R'" are selected from H, $C_{1-18}$ alkyl or alkenyl group., a substituted or unsubstituted phenyl, alkylphenyl or alkenyl phenyl group. It is important for the efficiency and stability of the peracid precursors according to the present invention that R', R" and R'" should not all be H in a given molecule. Preferably, R',R" and R'" are selected from H or a $C_{1-4}$ alkyl or alkenyl group. Most preferably, R',R" and R'" are methyl or ethyl.

Though not preferred, it is also possible to use acylated citrate which are only partially esterified, i.e. R', R" or R'" or combinations thereof are H, the only proviso being that not all three of R', R" and R'" can be H in a given molecule In the case where only one of R', R" and R'" is H, i.e. the acylated citrate ester is a diester, it is preferred to have a "central" diester, i.e. it is preferred that R" is not H In the case where two of R', R" and R'" are H, i.e. the acylated citrate ester is a monoester, it is preferred to have a symmetrical monoester i.e. a central monoester, i.e it is preferred that R" is not H. In case where monoesters are used, it is preferred that the ester chain be rather long, i.e up to 18 carbon atoms. The citrate ester thus acts as a precipitating builder.

Mixtures of said activators can also be used according to the present invention.

The most preferred compounds according to the present invention are acetyl triethyl citrate and octanoyl trimethyl citrate, preferably the former.

Some of the compounds according to the present invention are commercially available, such as acetyl triethyl citrate which is preferred herein. Other compounds can be synthesized by methods which are well known from the man skilled in the art. The synthesis of octanoyl trimethyl citrate is hereinafter described as an example.

2) Granular compositions comprising the acylated citrate esters

The acylated citrate esters according to the present invention can be used in granular compositions. As some of the compounds according to the present invention are liquid, for instance acetyl triethyl citrate, it may be necessary to absorb such liquid compounds onto solid substrates such as porous silicates, talc, starch, or crosslinked polymeric absorbants, or encapsulate them, for instance in microorganisms such as yeast such as described in EP 242 135, or include them in solid complexes such as those formed with cyclodextrines, for use in a granular composition. Such means to incorporate liquid compounds in granular products have been extensively described in the art and will not be further detailed herein.

Such granular products can be formulated without any hydrogen peroxide generating compound, as activating compositions to be used in combination with a second composition comprising hydrogen peroxide or a hydrogen peroxide generating compound. As an alternative, granular products comprising the acylated citrate esters according to the present invention can also be formulated which comprise a hydrogen peroxide generating compound. Such hydrogen peroxide generating compound have been extensively described in the art and include various salts and forms of perborate, percarbonate and the like.

Granular compositions according to the present invention can also be formulated as conventional compositions or as so-called "concentrated" or "compact" compositions which have a higher bulk density, of at least 600 g/l. Therefore, granular compositions according to the invention may comprise, if any, as broadly as from 2% to 60% by weight of the total composition of a hydrogen-peroxide generating compound, preferably from 10% to 40%. The amount of hydrogen-peroxide generating compound will be adjusted depending on the exact use foreseen for a given composition. Fully formulated detergent compositions according to the present invention will tend to comprise lower amounts of said compounds, whereas compositions formulated as bleaching additives may comprise higher amounts of hydrogen peroxide generating compounds.

Identically, the granular compositions according to the present invention may comprise from 0.5% to 60% by weight of the total composition of an acylatred citrate ester according to the present invention, or mixtures thereof, preferably from 5% to 30% by weight of the total composition. Here also, the optimum amount of acylated citrate ester will be adjusted depending on the intended use for the composition which is being formulated. Examples of such compositions are provided hereinafter.

Such granular products will likely comprise a filler material such as sodium or potassium sulfate or chloride or carbonate. Depending on the use for which the product is intended, the product may comprise additional ingredients. For instance, in a laundry detergent context, it is desirable to include in the product such ingredients as surfactants, buffering agents, soil release agents, soil suspending agents and enzymes, all of which have been extensively described in the art. It may also be desirable to include builders although the acylated citrate esters of the present invention provide building capacity, fluorescent whitening agents, and other ingredients well known in the art.

2) Liquid compositions comprising the acylated citrate esters

In a preferred embodiment of the present invention, the acylated citrate esters according to the present invention are used in liquid aqueous compositions. In this case also, liquid compositions can be formulated without hydrogen peroxide, to be used as activating compositions, or with hydrogen peroxide, as activated bleaching compositions. In both cases, the acylated citrate esters according to the present invention are particularly useful as they exhibit superior hydrolytical stability. For optimum stability, liquid compositions must be formulated and buffered in the mildly acidic range, i.e. with a pH as is of from 1 to 6, preferably from 3 to 5. Appropriate buffering of the compositions can be provided by organic or inorganic acids which are stable to oxidation; suitable acids are for instance adipic acid, tartaric acid, glutaric acid, phosphoric acid, succinic acid and citric acid. Most preferred is citric acid. Such liquid compositions are remarkably stable upon storage in that little activator loss occurs, as well as little available oxygen loss. Upon use in a laundry operation, the pH of the wash medium raises, mainly by dilution, and the system reacts efficiently to yield peracid. The composition according to the present invention will also often be used in a wash liquor which comprises a detergent composition which, itself, provides alkalinity. Effective laundry bleaching is thus obtained. In a non-laundry application, less peracid is generated, thus it is more the disinfectancy benefits which are obtained rather than an important bleaching effect. Liquid aqueous compositions according to the present invention can thus be used for the bleaching of laundry as well as for disinfecting hard surfaces.

Liquid aqueous compositions according to the present invention comprise from 0.5% to 50% by weight of the total composition of an acylated citrate ester according to the present invention, or mixtures thereof, preferably from 2% to 20%.

Activated liquid aqueous bleaching compositions according to the present invention comprise from 0.5% to 30% by weight of the total composition of hydrogen peroxide, preferably from 2% to 20%. The optimum levels of acylated citrate ester and hydrogen peroxide as well as the ratio of acylated citrate ester to hydrogen peroxide will be adjusted so as to obtain the desired bleaching performance.

As some of the acylated citrate esters according to the present invention are poorly soluble in water, it may be appropriate to include a solvent system in the composition, with a view to improve the solubility of the acylated citrate ester in the composition. Such solvent systems typically comprise alcohols.

The liquid aqueous compositions according to the present invention may further comprise hydrogen peroxide stabilizers such as stannates, pyrophosphates, chelants such as EDTA and NTA, radical scavengers such as BHT, and the like.

As for dry compositions described herein before, the liquid aqueous compositions according to the present invention may also comprise conventional ingredients, depending on the use intended for such compositions. Such conventional ingredients include surfactants, enzymes, builders, soil release agents, dyes, opacifiers, perfumes and other minors. Surfatcants are particularly desirable as they help to solubilize certain acylated citrate esters according to the present invention such as Acetyl triethyl citrate, which are hardly soluble in water.

EXAMPLES

The following examples will illustrate the present invention; they are not meant to restrict the scope of the present invention.

Example 1

Synthesis of Octanoyl Trimethyl Citrate

Trimethyl citrate (11.81 g; 0.05 mole) was dissolved at 50° C. in a mixture of dry pyridine (4.35g; 0.055 mole) and toluene (50 ml). Octanoyl chloride (8.95 g; 0.055 mole) was mixed with further toluene (10 ml) and added dropwise with stirring and the resulting suspension was maintained at 65° C. overnight. After filtration, the liquors were washed with acid (5% HCl) and water, dried ($Na_2SO_4$) and evaporated to dryness to yield the required (NMR-spectroscopy) ester (12.05 g; 67% yield) as a pale yellow oil.

The NMR resonance assignments were as follows:

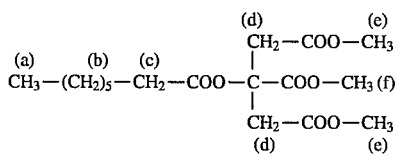

$^1$H assignments (from TMS): (a) 0.88,t; (b) 1.31,m; (c) 2.35,t; (d) 3.17,s; (e) 3.61,s; (f) 3.65,s, TLC chromatography (Merck G60 plates, chloroform solvent, dichlorofluorescein visualisation) revealed the ester as a single spot $R_f$0.43.

A perhydrolysis of this material (0.2%) at 40° C. in a standard heavy-duty detergent product solution (1%; Ariel Ultra®) containing sodium perborate tetrahydrate (0.3%) and ethylenediaminetetramethylphosphonate (40 ppm), as measured by titration with thiosulfate, gave 55% of the theoretical yield of peroctanoic acid in 30 minutes.

Example 2

Granular Detergent Composition

Acetyl triethyl citrate (ATC) was encapsulated in yeast cells in the manner described in EP242135 (AD2 limited) to a loading of 53% by weight. The resultant free flowing solid capsules were incorporated into the following granular detergent composition:

| Ingredient | % by weight |
|---|---|
| Linear alkyl benzene sulfonate | 7.9 |
| Fatty alcohol sulfate | 2.1 |
| Dobanol 45/E7 | 2.8 |
| Acrylic/Maleic Copolymer | 3.5 |
| Zeolite | 21.6 |
| Citrate/Citric Acid | 10.5 |
| Sodium Silicate | 1.0 |
| Chelant | 0.7 |
| Suds Suppressor | 1.7 |
| Sodium Perborate monohydrate | 11.3 |
| Acetyl triethyl Citrate capsules | 19.8 (= 10.5 ATC) |
| Protease | 1.2 |
| Perfume | 0.3 |
| Miscellaneous | 15.6 |

A perhydrolysis of this detergent composition, as measured by titration with thiosulfate, gave the theoretical yield of peracetic acid in less than 15 minutes.

Example 3

Alkaline Granular Bleach Booster

Encapsulated acetyl triethyl citrate (ATC) (as described above) was incorporated into the following granular bleach booster composition:

| Ingredient | % by weight |
|---|---|
| Linear alkyl benzene sulfonate | 18.6 |
| Citrate | 24.9 |
| Chelant | 1.7 |
| Carbonate | 7.8 |
| ATC Capsules | 47 |

On addition to a 1% solution of a typical granular detergent containing perborate monohydrate the theoretical yield of peracetic acid, as measured by titration with thiosulfate, was generated in less than 15 minutes.

Example 4

Acid Granular Bleach Booster

Encapsulated acetyl triethyl citrate (as described above) was incorporated into the following granular bleach booster composition:

| Ingredient | % by weight |
|---|---|
| LAS | 18.6 |
| Citric acid | 24.9 |
| Chelant | 1.7 |
| Carbonate | 7.8 |
| ATC Capsules | 47 |

On addition to a 1% solution of a typical granular detergent containing perborate monohydrate the theoretical yield of peracetic acid, as measured by titration with thiosulfate, was generated in less than 15 minutes.

Example 5

Granular Bleach Additive

Encapsulated acetyl triethyl citrate (as described above) was incorporated into the following granular bleach additive composition.

| Ingredient | % by weight |
| --- | --- |
| Percarbonate | 30 |
| ATC Capsules | 40 |
| Linear alkyl benzene sulfonate | 10.5 |
| Citrate | 14.1 |
| Carbonate | 4.4 |
| Chelant | 1.0 |

On addition to a 1% solution of a bleach-free granular detergent, the theoretical yield of peracetic acid, as measured by titration with thiosulfate, was generated in less than 15 minutes.

Examples 6–10

Liquid Compositions

|  | 6 | 7 | 8 | 9 | 10 |
| --- | --- | --- | --- | --- | --- |
| Hydrogen peroxide | 6.0 | 6.0 | 6.0 | 6.0 | 5.0 |
| Sodium Alkyl Sulphate | 8.0 | 8.0 | 8.0 | 8.0 | — |
| HLAS | 8.0 | 8.0 | 6.0 | — | 7.0 |
| ATC | 2.0 | 4.0 | 4.0 | 3.5 | 4.0 |
| Citric Acid | 1.0 | 1.0 | 1.0 | 0.5 | 1.0 |
| Isopropanol | — | 7.0 | 6.0 | — | — |
| Hexanol | — | 5.0 | 5.0 | — | — |
| NaOH | pH 4 | pH 4 | pH 4 | pH 4 | pH 4 |
| Water and minors | | | up to 100% | | |

Compositions 6, 7 and 8 were monitored for stability. Both the available oxygen and the activator activity were measured in the fresh compositions, and in the compositions after 2 weeks storage at 50° C. The results are expressed in % loss. The available oxygen was measured by permanganometric titration wherein the titration end point was detected potentiometrically by a Pt electrode. The relative AvO is determined by the expression: % AvO loss= 100*(AvO(fresh)−AvO(aged))/AvO(fresh). The activator activity was measured by titrating (with NaOH, end point of titration is determined potentiometrically by a combined glass electrode) the total acidity of the fresh and aged products. The assumption is made that the acidity increase is entirely due to the activator hydrolisis. Thus the number of moles of acid procuced equals the number of moles of activator hydrolysed. The relative activator loss is determined by the expression: %Activator loss=100*(moles acid-(aged)−moles acid(fresh)/moles ATC.

| STABILITY DATA | | |
| --- | --- | --- |
|  | Relative AvO loss (%) after 2 weeks at 50° C. | Relative activator loss (%) after 2 weeks at 50° C. |
| 6: | 7.8 | 15.0 |
| 7: | 5.4 | 10.0 |
| 8: | 8.7 | 7.5 |

These results show that these compositions are stable, both in terms of available oxygen and in terms of activator stability, even under stressed storage conditions.

PERFORMANCE DATA

Composition 1 hereinabove was compared to the same composition without ATC for laundry bleaching performance, on top of DASH® powder in a launderometer test, both at 40° C. and 60° C. The results were:
(Results expressed as psu)

| Temperature | 40° C. | 60° C. |
| --- | --- | --- |
| coffee | 1.0s | 0.8 |
| tea | 2.4s | 1.3s |
| wine | 0.6 | 0.3 |
| cocoa | 0.8 | 0.4 |

These results show a significant bleaching benefit on bleachable stains such as tea stains, especially at low temperatures such as 40° C. where conventional bleaching systems are usually less efficient.

What is claimed is:

1. A method for bleaching or disinfecting fabric, said method comprising the step of contacting fabric in need of bleaching or disinfection with an aqueous solution comprising:

a) a peracid precursor having the formula:

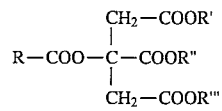

wherein R is selected from the group consisting of $C_1$–$C_9$ alkyl, $C_1$–$C_9$ alkenyl, phenyl, sulpho-substituted phenyl, alkylphenyl, alkenylphenyl, and mixtures thereof; R' is selected from the group consisting of hydrogen, $C_1$–$C_{18}$ alkyl, $C_1$–$C_{18}$ alkenyl, phenyl, sulpho-substituted phenyl, alkylphenyl, alkenylphenyl, and mixtures thereof; R" is selected from the group consisting of hydrogen, $C_1$–$C_{18}$ alkyl, $C_1$–$C_{18}$ alkenyl, phenyl, sulpho-substituted phenyl, alkylphenyl, alkenylphenyl, and mixtures thereof; R'" is selected from the group consisting of hydrogen, $C_1$–$C_{18}$ alkyl, $C_1$–$C_{18}$ alkenyl, phenyl, sulpho-substituted phenyl, alkylphenyl, alkenylphenyl, and mixtures thereof; provided that R', R", and R'" are not all hydrogen; and mixture of said peracid precursor; and b) a source of hydrogen peroxide selected from the group consisting of hydrogen peroxide, a hydrogen peroxide generating compound, and minutes thereof;

and wherein said peracid precursor and said source of hydrogen peroxide are individually employed in an amount sufficient to react together to form an effective amount of peracid to bleach or disinfect the fabric.

2. A method according to claim 1 wherein R is methyl or heptyl.

3. A method according to claim 1 wherein R', R", and R'" are selected from the group consisting of hydrogen, a $C_{1-4}$ alkyl, or a $C_{1-4}$ alkenyl group.

4. A method according to claim 1 wherein R', R", and R'" are independently selected from hydrogen, methyl, and ethyl groups.

5. A method according to claim 1 wherein the peracid precursor is selected from acetyl triethyl titrate, octanoyl trimethyl citrate, and mixtures thereof.

6. A bleaching or disinfecting composition comprising:

a) a peracid precursor having the formula

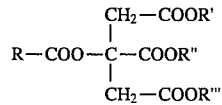

wherein R is selected from the group consisting of $C_1$–$C_9$ alkyl, $C_1$–$C_9$ alkenyl, phenyl, sulpho-substituted phenyl, alkylphenyl, alkenylphenyl, and mixtures thereof; R' is selected from the group consisting of hydrogen, $C_1$–$C_{18}$ alkyl, $C_1$–$C_{18}$ alkenyl, phenyl, sulpho-substituted phenyl, alkylphenyl, alkenylphenyl, and mixtures thereof; R" is selected from the group consisting of hydrogen, $C_1$–$C_{18}$ alkyl, $C_1$–$C_{18}$ alkenyl, phenyl, sulpho-substituted phenyl, alkylphenyl, alkenylphenyl, and mixtures thereof; R'" is selected from the group consisting of hydrogen, $C_1$–$C_{18}$ alkyl, $C_1$–$C_{18}$ alkenyl, phenyl, sulpho-substituted phenyl, alkylphenyl, alkenylphenyl, and mixtures thereof; provided that R', R", and R'" are not all hydrogen; and mixture of said peracid precursor;

b) a source of hydrogen peroxide selected from the group consisting of hydrogen peroxide or a hydrogen peroxide generating compound; and c) one or more conventional detergency ingredients selected from the group consisting of surfactants, buffering agents, soil release agents, soil suspending agents, enzymes, builders, dyes, perfumes, opacifiers, hydrogen peroxide stabilizers, and fluorescent whitening agents;

wherein said peracid precursor and said source of hydrogen peroxide are individually employed in an amount sufficient to react together in an aqueous solution to form an effective amount of peracid to bleach or disinfect a substrate.

7. A composition according to claim 6 wherein R is methyl or heptyl.

8. A composition according to claim 6 comprising from 0.5% to 30% by weight of the total composition of hydrogen peroxide.

9. A composition according to claim 6 comprising from 2% to 60% by weight of the total composition of a hydrogen peroxide generating compound.

10. A composition according to claim 6 wherein R', R", and R'" are selected from the group consisting of hydrogen, a $C_{1-4}$ alkyl, or a $C_{1-4}$ alkenyl group.

11. A composition according to claim 10 wherein R', R", and R'" are selected from hydrogen and methyl groups.

12. A composition according to claim 11 comprising from 0.5% to 30% by weight of the total composition of hydrogen peroxide.

13. A composition according to claim 11 comprising from 2% to 60% by weight of the total composition of a hydrogen peroxide generating compound.

14. A composition according to claim 10 wherein R', R", and R'" are selected from hydrogen and ethyl groups.

15. A composition according to claim 14 comprising from 0.5% to 30% by weight of the total composition of hydrogen peroxide.

16. A composition according to claim 14 comprising from 2% to 60% by weight of the total composition of a hydrogen peroxide generating compound.

17. A composition according to claim 6 wherein the peracid precursor is selected from acetyl triethyl citrate, octanoyl trimethyl citrate, and mixtures thereof.

18. A composition according to claim 17 comprising from 0.5% to 30% by weight of the total composition of hydrogen peroxide.

19. A composition according to claim 17 comprising from 2% to 60% by weight of the total composition of a hydrogen peroxide generating compound.

* * * * *